United States Patent [19]

Draper

[11] Patent Number: 5,004,810

[45] Date of Patent: Apr. 2, 1991

[54] ANTIVIRAL OLIGOMERS

[75] Inventor: Kenneth G. Draper, Madison, N.J.

[73] Assignee: Schering Corporation, Kenilworth, N.J.

[21] Appl. No.: 252,225

[22] Filed: Sep. 30, 1988

[51] Int. Cl.$^5$ .................. C07H 15/12; C07H 47/00
[52] U.S. Cl. ........................................ 536/27; 536/28
[58] Field of Search ............... 536/27, 28, 29; 514/44

[56] References Cited

U.S. PATENT DOCUMENTS 4,689,320 8/1987 Kaji ....................................... 536/27
4,757,055 7/1988 Miller et al. .

FOREIGN PATENT DOCUMENTS 8301451 4/1983 PCT Int'l Appl. .
2148302 5/1985 United Kingdom .

OTHER PUBLICATIONS

Dalrymple et al., Nucleic Acids Res. 13:7865 (1985).
Dalrymple, M. A., Nucleic Acid Res., Nov. 11, 1985, 13(21), pp. 7865-7879.
Gelman et al., Proc. Natl. Acad. Sci., U.S.A., 82:5265 (1985).
Gordon et al., Invest. Opthalmol. Visual Sci. 29:157 (1988).
Smith et al., Proc. Natl. Acad. Sci., U.S.A., 83:2787 (1986).
Toulme, La Recherche, vol. 18, No. 184 (1987).
Zamecnik et al., Proc. Natl. Acad. Sci., U.S.A., 75:280 (1978).
Zamecnik et al., Proc. Natl. Acad. Sci., U.S.A., 83:4143 (1986).
Smith et al., Proc. Natl. Acad. Sci., U.S.A., 83:2787-91 (1986).
Zamecnik et al., Proc. Natl. Acad. Sci., U.S.A., 83:4143-46 (1986).
Stephenson et al., Proc. Natl. Acad. Sci., U.S.A., 95:285-88 (1978).
Mizuno et al., Proc. Natl. Acad. Sci., U.S.A., 81:1966-70 (1984).
Melton et al., Proc. Natl. Acad. Sci., U.S.A., 82:144-8 (1985).
Blake et al., Biochemistry, 24:6132-145 (1985).
Maher and Dolnick, Nacleic Acids Res., 16:3341-58 (1988).

Primary Examiner—Robert A. Wax
Assistant Examiner—Bradley L. Sisson
Attorney, Agent, or Firm—Norman C. Dulak; James R. Nelson

[57] ABSTRACT

Oligomers that are complementary in base sequence to the initiation region on mRNA coding for herpes simplex virus transactivating proteins inhibit the replication of the virus.

3 Claims, 2 Drawing Sheets

ANTIVIRAL OLIGOMERS

BACKGROUND OF THE INVENTION

A number of studies have shown that various oligonucleotides that are complementary to DNA or RNA (including mRNA) can hybridize to the genetic material and inhibit transcription, replication or translation.

It has been shown by Smith et al., Proc. Natl. Acad. Sci. U.S.A., 83: 2787–91 (1986) that an eight residue oligomer complementary to the acceptor splice junction of Herpes Simplex Virus-1 (HSV-1) immediate early mRNAs 4 and 5 inhibits viral replication with little, if any, deleterious effect on host-cell macromolecular metabolism and growth rate. It has also been shown that sequences that are complementary to regions immediately adjacent to the tRNA Lys primer binding site in human T-cell lymphotropic virus type III (HTLV-III) inhibited replication of the virus [Zamecnik et al., Proc. Natl. Acad. Sci. U.S.A., 83: 4143–6 (1986)]. Similar inhibition was seen in the same study when the oligomers were complementary to a splice donor site or a splice acceptor site. The seven oligomers of the Zamecnik et al. study varied in size from 12 to 26 bases. In another study, a 13-mer (an oligomer containing 13 repeating units) that is complementary to the reiterated terminal sequence of Rous sarcoma virus (RSV) 70s RNA inhibits the production of RSV with the proposed mechanism of inhibition being either in the circularization step of the proviral DNA intermediate and/or in the initiation of translation [Stephenson and Zamecnik, Proc. Natl. Acad. Sci. U.S.A., 75: 285-4 (1978)]. U.S. Pat. No. 4,757,055 discloses certain oligonucleoside alkyl and aryl phosphonates that are complementary to base sequences "foreign" to mammalian cells and that hinder the replication and/or translation of such foreign base sequences. The foreign sequences relating to HSV relate to the acceptor splice junction (column 23, lines 12–14).

European Patent Application No. 263740 discloses RNA and DNA sequences that are complementary to the ribosome binding site of mRNAs, and to sites that are critical to viral RNA polymerase binding (page 4, lines 57 through 64). The various sequences disclosed are postulated to have antiviral effects.

In non-viral systems, inhibition of translation has been postulated to occur in various systems. Expression of the genes coding for the major outer membrane proteins in *E. coli* is inhibited by a 174-base mRNA (referred to as mRNA—interfering complementary RNA or micRNA) that is transcribed by the *E. coli* and that contains a sequence that is complementary to the 5' end region of the membrane protein mRNAs [Mizuno et al., Proc. Natl. Acad. Sci. U.S.A., 81: 1966–70 (1984)]. In frog oocytes, microinjection of RNA complementary to globin mRNA (anti-sense globin RNA) formed a hybrid with globin mRNA and selectively prevented translation [Melton, Proc. Natl. Acad. Sci. U.S.A., 82: 144–8 (1985)]. In rabbits, inhibition of rabbit globin mRNA translation by oligonucleotides complementary to the 5' end region has been observed [Blake et al., Biochemistry, 24: 6132–45 (1985)].

Non-ionic versions of complementary oligodeoxyribonucleoside methylphosphonates were shown to inhibit translation of dihydrofolate reductase (DHFR) to a lesser extent than the corresponding oligodeoxyribonucleotides [Maher and Dolnick, Nucleic Acids Res., 16: 3341–58 (1988)].

In HSV (herpes simplex virus) one of the factors affecting selective initiation of alpha phase gene transcription is a transactivating virion component, the Vmw65 protein [J. Mol. Biol., 180:1–19 (1984)]. Some transactivating virion components, including Vmw65, may be produced from the viral genetic material and stored in new virus particles. After invasion of a new host cell by these virus particles, the transactivating components interact with certain regions of the viral DNA sequences and stimulate transcription of the adjacent downstream genes, which code for proteins needed by the virus for replication. Optimal activation by Vmw65 requires specific DNA structural elements, including an activation-response DNA sequence recognized by the Vmw65 protein. This activation-response DNA sequence is situated usually near the alpha phase promoter so that recognition of the activation-response DNA sequence by the transactivating Vmw65 protein stimulates transcription of the gene located downstream from the alpha phase promoter. A number of proteins found in Herpes Simplex Virus have similar transactivating potential when their corresponding activation-response DNA sequences are located upstream from target genes. These proteins include the proteins ICP4, ICP0 and ICP27, which are described in Everett, J. Gen. Virol. 67:2507–13(1986); and Rice and Knipe, J. Virol. 62(10):3814–23 (1988). Similar transactivating mechanisms exist, for example, in the Pseudorabies virus (PRV-IE gene product), Adenovirus (Ad-EIA) and Human cytomegalovirus (HCMV-MIE protein).

Interference with or disruption of the viral transactivating mechanism could ultimately result in the inhibition of viral replication. To test this theory I have invented a method whereby the normal translation of certain target transactivating proteins is prevented. The results of the practice of this method, which are reported herein, demonstrate that inhibition of viral replication has been accomplished.

SUMMARY OF THE INVENTION

The present invention involves an inhibitor of HSV replication comprising an oligomer containing bases selected from the group consisting of adenine, guanine, cytosine, thymine and uracil, wherein said oligomer is capable of sufficient hybridization to the initiation region of the messenger RNA coding for a HSV transactivating protein so as to prevent normal translation of said transactivating protein.

A preferred embodiment of the inhibitor has the sequence:

3'                                    5'
CGG CTG TAC CTG CGC CTG

A pharmeceutical composition aspect of the present invention involves a pharmeceutical composition comprising a translationally inhibiting effective amount of an inhibitor disclosed herein in combination with a pharmaceutically acceptable carrier.

A method aspect of the present invention involves treating a host infected with, or at a risk of being infected with HSV comprising providing to said host a translationally inhibiting amount of the inhibitor disclosed herein.

DETAILED DESCRIPTION OF THE INVENTION

Figure 1:
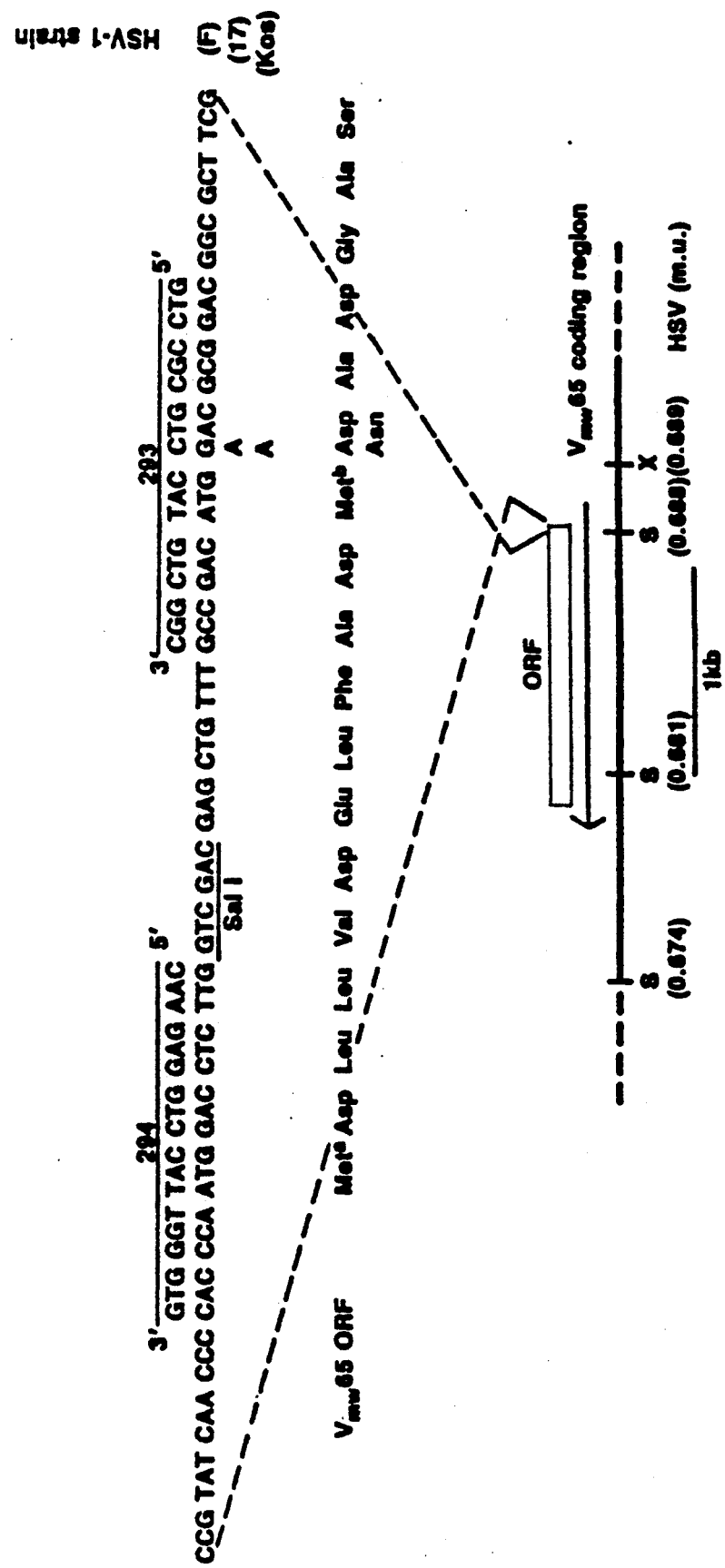
FIG. 1 is a schematic of the Vmw65 gene region. Selected restriction map of the HSV-1 region encoding the Vmw65 gene is illustrated at the bottom of the figure. The location of the Vmw65 mRNA and direction of transcription on the prototypical arrangement of the HSV-1 genome are depicted by an arrow. The open reading frame (ORF) of the Vmw65 protein is presented as a rectangle and the DNA sequence spanning the region which encodes the translation initiation codon(s) of the Vmw65 ORF are shown. The DNA sequence is taken from the F strain of HSV-1 as determined by Pellett et al., Proc. Natl. Acad. Sci. U.S.A., 82m:5870 (1985). The single nucleotide change present in the strain 17 [Dalrymple et al., Nucleic Acids Res., 13:7865 (1985)] and KOS genes are shown, as is the predicted amino acid content of the N terminal regions of the Vmw65 polypeptide products. For reference, the Sal I site at 0.688 map units (m.u.) is shown under the nucleotide sequence. The nucleotide sequences of complementary oligodeoxyribonucleotides 293 and 294 are shown above their respective regions of complementarity, X, Xho I restriction site; S, Sal I restriction site.

The oligomers of the present invention are a sequence of bases selected from adenine (A), guanine (G), cytosine (C), thymine (T) and uracil (U). Such bases are linked via a backbone such that the bases remain approximately 3.0 to 4.0 Å apart, preferably about 3.4 Å apart, which is the normal distance between bases found in ribonucleic acid (RNA) and deoxyribonucleic acid (DNA), or any other chemical linkage that would displace the bases the desired distance from each other that would allow the necessary rotation to provide the helical configuration found in most native oligonucleotides. Such linking backbones include ribose phosphate, deoxyribose phosphate, ribose alkylphosphonate, deoxyribose alkylphosphonate, [Maher et al., Nucleic Acids Res., 16:3341 (1988); Smith et al., Proc. Natl. Acad. Sci. U.S.A., 83:2787 (1986); Blake et al., Biochemistry, 24:6132 (1985)], ribose arylphosphonate, deoxyribose arylphosphonate [U.S. Pat. No. 4,757,055]. The existence and preparation of oligomers utilizing the linkages described herein are well known to those skilled in the art and include phosphorothioates [Marcus-Sekura et al., Nucleic Acids Res. 15:5749-62 (1987)]; phosphorodithioates [Nielsen et al., Tetrahedron Letters 29:2911-14 (1988)]; phosphoroselenoates, phosphoroamidates and alkyl-phosphorotriesters [Koziolkiewicz et al., Chemica Scripta 26:251,-60 (1986); Gallo et al., Nucleic Acids Res. 14:7405-20 (1986); Stec et al., J. Am. Chem. Soc. 106:6077-79 (1984); Stec et al., J. Chromatogr. 326:263-80 (1985); Koziolkiewicz et al., Chemica Scripta 26:251-60 (1986); and La Planche et al., Nucleic Acids Res. 14:9081-93 (1986)]; and others [European Patent Application 263,740].

Preferably the linkages will be ribose phosphate, deoxyribose phosphate or deoxyribose alkylphosphonate, e.g., deoxyribose methylphosphonate. The use of complementary oligodeoxyribonucleotides is preferable to the use of oligoribonucleotides since some eucaryotic cells are known to possess a double stranded RNA specific unwindase activity that may result in the lessening of hybridization efficiency and the potential failure of inhibition of mRNA translation [Wagner and Nishikura, Mol. Cell. Biol., 8:770 (1988)]. Complementary oligodeoxyribonucleotides are susceptible in vivo to the activity of nonspecific exonuclease activity found in serum, particularly an exonuclease that appears to progressively digest oligomers from the 3' terminus. The use of methylphosphonate or other "blocked" derivatives may prevent nuclease digestion, but such oligomers do not appear to inhibit translational activity as effectively as their phosphodiester-linked analogs [see Maher and Dolnick, Nucleic Acid Res., 16:3341 (1988)]. As a result, the more preferred linkages are the deoxyribose derivatives, e.g., deoxyribose phosphate and deoxyribose alkylphosphonate, and the particular deoxyribose derivative utilized will depend on the particular circumstances of the system sought to be inhibited. For example, a non-serum containing system or a serum system in which exonuclease activity can be chemically blocked would favor the deoxyribose phosphate linkage, whereas strong exonuclease activity would favor the deoxyribose alkylphosphonate linkage. The most preferred deoxyribose alkylphosphonate is deoxyribose methylphosphonate.

As used herein the following terms have the designated meaning unless otherwise indicated:

alkyl—represents straight or branched hydrocarbon chains having from 1 to 6 carbon atoms; and aryl—represents an unsaturated hydrocarbon ring having from 6 to 15 carbon atoms and sufficient conjugated double bonds or pi electron characteristics to impart aromatic character, preferably containing at least one benzenoid ring.

Hybridization in the context of the present invention is meant to include hydrogen bonding between complementary base pairs. Guanine and cytosine are known to form three hydrogen bonds between them while adenine and thymine and adenine and uracil are known to form two hydrogen bonds between them. The precise sequences of the synthethic inhibitor and of the complementary strand will determine the fidelity and strength of the hybridization and the resultant inhibition of translation of the hybridized mRNA.

Sufficient hybridization must occur for inhibition of translation to occur. Sufficient hybridization relates to the strength of the hydrogen bonding as well as the specificity of the complementary oligomer. The strength of the hydrogen bonding is influenced by the number and percentage of bases in an oligomer that are base paired to complementary bases. To be specific, the complementary bases of the oligomer must be sufficient in number so as to avoid non-specific binding to other sequences within a genome while at the same time small enough in number to avoid non-specific binding between other sequences within a genome and portions of a long oligomer. For example, the human genome contains approximately $3 \times 10^9$ bases in its genome. Since any single base can be chosen from the four bases (C,G,A and T or U), an oligomer of length X has the possibility of $4^x$ possible sequences. A 15 base oligomer has $1.07 \times 10^9$ possible sequences and a 16 base oligomer has $4.3 \times 10^9$ possible sequences suggesting a lower limit for the length of a uniquely occurring sequence. Above about 30 bases in length, an oligonucleotide would likely contain a section of about 15 bases which would have a complementary strand somewhere in the targetted genome other than the targetted protein mRNA and such a 15 base oligomer would be about 50% of the 30 base oligomer. Consequently, the upper limit on a potential oligomer would be about 30 bases. Of course, it will be appreciated that a longer oligomer may be able to specifically hybridize if a portion of the oligomer is internally complementary and able to hybridize to itself. This would result in a hybridized inert lobe flanked on either or both sides by exposed bases, which bases are capable of hybridizing to the initiation region of the HSV transactivating protein region that is the target of the present invention.

Consequently, the oligomers of the present invention are preferably 15 to 30 bases in length, more preferably 15 to 25 bases in length and most preferably 16 to 18 bases in length. The oligomers, when they are oligonucleotides, are preferably prepared using commercially available sequencers such as an Applied Biosystems Synthesizer Model 280A. The oligonucleotides may also be organically synthesized as described in Maher and Dolnick, Nucleic Acids Res., 18:3341 (1988) and Miller et al., Nucleic Acids Res. 11, 6225 (1983). It will also be appreciated that the oligonucleotides may be produced by recombinant DNA techniques and purified by methods that are known to those skilled in the art. Oligomers containing other types of linkages may be prepared as described in European Patent Application No. 263,740; Marcus-Sekura et al., Nucleic Acids Res. 15:5749-62 (1987) (phosphorothioates); Neilsen et al., Tetrahedron Letters 29:2911-14 (1988) (phosphorothioates); Koziolkiewicz et al., Chemica Scripta 26:251-60 (1986), Gallo et al., Nucleic Acids Res. 14:7405-20 (1986), Stec et al., J. Am. Chem. Soc. 106:6077-79 (1984), Stec et al., J. Chromatogr. 326:263-80 (1985), Koziolkiewicz et al., Chemica Scripta 26:251-60 (1986) and La Planche et al., Nucleic Acids Res. 14:9081-93 (1986) (phosphoroselenoates, phosphoroamidates and alkyl phosphotriesters) or by other techniques known to those in the art.

It will also be appreciated that the base sequence of the oligomer need not be 100% complementary to the sequence to which it is targetted to hybridize. Preferably the sequence will be at least 70% complementary, more preferably at least 80% and even more preferably at least 90%. The oligomer need only be capable of sufficient hybridization to the initiation region of the mRNA coding for an HSV transactivating protein so as to prevent normal translation of said transactivating protein. Prevention of normal translation of a transactivating protein occurs when the transactivating protein itself is produced in an amount significantly lower than would be the result in the absence of the inhibiting oligomer. Measurement of the decrease in production of proteins is well known to those skilled in the art and would include quantification by chromatography, biological assay or immunological reactivity. A preferred method of measuring the effect of an inhibiting oligomer is to genetically engineer a biologically active gene downstream from the promoter/enhancer (activation-response DNA sequence) that is activated by the transactivating protein. Therefore, a decrease in the production of the transactivating factor will result in a decrease in the amount of mRNA that is associated with the transactivated promoter/enhancer and a subsequent decrease in the amount of enzyme encoded by this mRNA. A particularly preferred biologically active protein would be an enzyme e.g., $\beta$-galactosidase, that conveniently produces a detectable product in the presence of an indicator, e.g., 5-bromo-4-chloro-3-$\beta$-O-galactopyranoside and methylumbelliferyl-$\beta$-D-galactopyranoside. Such genetic engineering techniques are known to those skilled in the art and are further described in PCT Application U.S. 88/00680.

The transactivating proteins inhibited by the practice of the present invention are any of the HSV transactivating proteins that have the ability to recognize an activation-response DNA sequence and stimulate the transcription of the adjacent downstream genes. Preferably the transactivating protein is an alpha phase transactivating factor, more preferably Vmw65 [J. Mol. Biol. 180:1-19 (1984)], ICP4 [Everett, J. Gen. Virol 67:2507-13 (1986)], ICP0 [Everett, J. gen. Virol. 67:2507-13 (1986)] or ICP27 [Rice and Knipe, J. Virol. 62:3814-23 (1988)] and most preferably Vmw65. HSV or herpes simplex virus includes both HSV-1 and HSV-2 virus, preferably HSV-1.

The initiation region of the transactivating proteins is any sequence containing the ATG initiation codon within the gene coding for the transactivating protein, preferably any sequence up to 30 bases. Preferably the ATG codon is located near the 5' end of said transactivating-gene, although not necessarily the ATG codon nearest the 5' end.

As has been alluded to previously, the oligomers of the present invention will optimally have certain characteristics, among them: (1) the ability to enter living cells that are susceptible to being infected with HSV virus; (2) resistance to enzymatic degradation or hydrolysis; and (3) the ability to form sufficiently stable complexes with complementary base sequences.

In practicing the method aspect of the present invention, one introduces an inhibitory oligomer to cells infected or at risk of being infected with HSV. Additionally one may provide a penetration enhancer to the solution to facilitate uptake of the oligomer by the infected or susceptible cells or provide a leader sequence to facilitate uptake of the oligomer by the infected cells. Additionally, one may conjugate the oligomer to a carrier molecule to facilitate uptake of the oligomer by the infected cell. One may also add inhibitors of degradation enzymes, denaturing enzymes, etc., e.g., unwindase, to increase the longevity of the inhibiting oligomer and the fidelity of the hybridization. Using estimates of RNA levels from dot blots and estimates of oligomer levels from uptake studies in MTX5 cells, the preferable ratio of oligomer:transactivating protein mRNA is less than 1000:1, more preferably about 500 to 1000:1. Consequently, the amount of oligomer in a pharmaceutical composition may range from about 0.5 to about 5 percent by weight, more preferably about 0.5 to 2 percent by weight.

Any of the above components may be combined in a pharmaceutical composition. In addition to the above components, such a composition may also include buffers, carriers etc. The preferred pharmeceutical compositions are topical, such as creams, lotions or gels.

Depending on the severity of the viral infection, the present compositions may be administered one or more times per day for a period ranging from a few days to several months or until sufficient improvement is obtained, depending upon the judgment of the attending clinician.

Formulations for topical application, e.g., for use in treating skin sores, may include the liquid forms, creams, aerosols, sprays, dusts, powders, lotions and ointments which are prepared by combining an active ingredient according to this invention with conventional pharmaceutical diluents and carriers commonly used in topical dry, liquid, cream and aerosol formulations. Ointment and creams may, for example, be formulated with an aqueous or oily base with the addition of suitable thickening and/or gelling agents. For example, such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

Lotions may be formulations with an aqueous or oily base and will, in general, also include one or more of stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

For vaginal administration, the use of tablets, suppositories or coated condoms may also be advantageous.

The following examples serve to illustrate the invention without limiting it in any way.

EXAMPLE 1

Inhibition of In Vitro Translation from Vmw65 RNA by Complementary Oligodeoxynucleotide This example illustrates the formation of oligomer-mRNA hybrids and the effect, of such hybridization upon translation of the mRNA into Vmw65 protein.

Materials and Methods

Cells and Virus

LTK-cells, originally from the American Type Culture Collection (CCL 1.3), were maintained in Eagles Minimal Essential Medium (EMEM) supplemented with glutamine, penicillin, streptomycin and 10% fetal calf serum. MTX5 cells [Kmetz et al., Nucleic Acids Res., 16:4935 (1988); PCT Application U.S. 88/00680] were selected, expanded and maintained in supplemented EMEM containing 1X hypoxanthine/aminopterine/thymidine (HAT) [Wigler et al., Cell, 14:725 (1979)]. Vero cells were maintained in Medium 199 containing glutamine, penicillin, streptomycin, 10 mM HEPES (N-2-hyroxyethylpiperazine-N'-2-ethanesulfonic acid, pH 8.0), and 5% fetal calf serum. Common, well known HSV-1 (strain KOS) and HSV-2 (strain MS available from ATCC VR-540) stocks were grown in Vero cells and harvested by standard procedures.

Plasmid Constructs

All restriction endonucleases and DNA ligase were purchased from New England Biolabs, Inc. Restriction endonuclease digestion and DNA fragment ligation were performed by established procedures [Maniatis et al., Molecular Cloning, A Laboratory Manual, Cold Springs Harbor Laboratory, U.S.A. (1982)] using buffers recommended by the manufacturer.

The HSV-1 Sal F' fragment (0.681–0.688 map units or mu), which contains the amino terminal 83% of the Vmw65 translational reading frame [Pellett et al., Proc. Natl. Acad. Sci. U.S.A., 82:5870 (1985)] was generated from plasmid Hind Bgl DG [0.647–0.698 mu, Hall et al., J. Virol., 43:594 (1982)] by digestion with Sal I restriction endonuclease. The 1.2 kilobase (kb) Sal F' fragment was separated from other DNA fragments by electrophoresis through 1% Low Melting Point agarose gels, extracted according to prescribed methods (Maniatis et al., 1982) and cloned into the Sal I site of the transcription vector pGEM-2 (Promega Biotech) to produce the recombinant plasmid pEM-2. The orientation of the Sal F' fragment within pEM-2 was determined by a double digestion with restriction enzymes Kpn I, which recognizes a unique site within the inserted fragment, and Bam H1.

Plasmid Hind Bgl DG was obtained from E. Wagner, University of California, Irvine, Calif. Plasmid pON 105, which contains the HSV-1 ICP4 promoter located immediately 5' of the E. coli lac Z gene, was obtained from E. Mocarski, Stanford University, Stanford, Calif.

Oligodeoxyribonucleotide Preparation

Oligodeoxyribonucleotide sequence, 5'-GTCCGCGTCCATGTCGGC (293) and 5'-CAAGAGGTCCATTGGGTG (294), which are complementary to the Vmw65 mRNA sequence spanning the putative translation initiation codons for the open reading frame of the HSV-1 Vmw65 protein, were synthesized on an Applied Biosystems Synthesizer Model 280A. Following synthesis, the oligodeoxyribonucleotides were treated with thiopohenol to remove methoxy groups on the phosphates, then cleaved from the silica support with ammonium hydroxide. Deprotection was completed by heating the oligomer in a 14.5M solution of ammonium hydroxide at 55° C. for 8–16 h. The solution was dried in a Speed Vac Concentrator (Savant), redissolved in water and extracted with n-butanol to remove benzamides formed during protection. The crude oligomer preparation was dried, resuspended in water, and electrophoresed on a denaturing polyacrylamide gel according to estabished procedures [Maxam and Gilbert, Methods Enzymol, 65:499 (1980)]. The oligomer bands were visualized by ultraviolet shadowing using a fluorescent thin layer chromatography (TLC) plate, then cut from the gel and eluted by overnight incubation at 37° C. in elution buffer (0.5 ammonium acetate, 10mM magnesium acetate). After desalting using a C-18 Sep-pak column (Waters), the concentration of oligomer was determined as A260 units in the solution.

In Vitro Transcription

Transcription reagents were obtained from Promega Biotech and protocols were performed as recommended by the manufacturer. To produce RNA (+strand) encoding the truncated Vmw65 reading frame, plasmid pEM-2 was linearized by digestion with Bam H1 and used as template for in vitro transcription with T7 RNA polymerase. Uniformly labeled complementary strand RNA (- strand) was prepared by transcription of pEM-2, linearized with Hind III, using SP6 polymerase in the presence of $^{32}$P-CTP (Amersham). In vitro transcripts were purified by digestion of template DNA with RQ1 D-Nase (20 min., 30° C.), two extractions with phenol:chloroform:isoamyl alcohol (24:24:1), extraction with chloroform:isoamyl alcohol (24:1), precipitation in 0.3M sodium acetate and 70% ethanol, and resuspension in 60 µl of diethyl pyrocarbonate (DEPC)-treated water.

In Vitro Translation/Hybrid Arrest

In vitro translation reagents were purchased from Promega Biotech and used according to manufacturer's specifications. Translation reactions contained 1 µg of pEM-2 transcribed RNA and 38 µl of translation cocktail in a total volume of 50 µl. (One ml of translation cocktail contains: 790 µl of rabbit reticulocyte lysate, 26 µl of a methionine-free amino acid mixture, 39 µl of Rnasin, 130 µl of $^{35}$S methionine [50uCi, 400 Ci/mmol, Amersham] and 15 µl of DEPC-treated water.) The translation mixture was incubated for 2 hr at 30° C., then digested for 20 min. at 37° C. with RNase A at a final concentration of 370 µg/ml. For hybrid arrest experiments, 1 µg of RNA was combined with an appropriate amount of oligodeoxyribonucleotide in DEPC-treated water to yield a total volume of 12 µl. This mixture was incubated at room temperature for 90 min. before addition to 38 µl of translation cocktail.

Analysis of In Vitro Translation Products

For determination of total $^{35}$S-methionine incorporation, the equivalent of 2 µl of translation mixture was added to 1 ml of a 1N NaOH/1.5% hydrogen peroxide solution and incubated at 37° C. for 10 min. Following the addition of 4 ml of cold 25% trichloroacetic acid (TCA)/2% casamino acids, samples were incubated on ice for 30 min., then filtered through Millipore AP filters. Filters were washed under vacuum with ethanol and acetone, air dried, and added to 4 ml of Aquasol (Dupont). TCA-precipitable counts were quantified in a Packard model 2000CA Liquid Scintillation Analyzer.

For analysis of Vmw65 specific translation product, the equivalent of 2 µl of translation mixture was diluted into an equal volume of 2x Laemmli Loading Buffer (1x=88 mM Tris-HCl, pH 6.8; 2% sodium dodecyl sulphate [SDS]; 5% beta-mercaptoethanol; 10% glycerol, and 0.001% bromphenol blue), heated in a boiling water bath for 5 min., and analyzed by electrophoresis in either a 10% polyacrylamide-SDS (Laemmli) gel or prepoured 10-20% polyacrylamide-SDS gel (Integrated Separation Systems). The resultant gels were dried under vacuum and autoradiography was performed using Kodak XAR-5 film.

S1Nuclease Analysis of RNA-Oligodeoxyribonucleotide Hybrid Formation

Oligodeoxyribonucleotide used for hybridization to pEM-2 transcribed RNA was end labeled with [γ-$^{32}$P]-ATP using T4 polynucleotide kinase (Bethesda Research Laboratories) according to published protocol [Maxam and Gilbert, Methods in Enzymol., 65:499 (1980)]. Hybridization solutions (13 µl) contained 1 µg of pEM-2 transcribed RNA and 1×10$^7$ cpm/ug of $^{32}$P end-labeled oligodeoxyribonucleotide (oligo 293) in water, either with 31 µg unlabeled oligo 293 (2000 fold molar excess of oligodeoxyribonucleotide) or without unlabeled oligo 293 (5 fold molar excess of RNA). A control for S1 nuclease activity contained only $^{32}$P end labeled oligo 293. The hybridization mixtures were incubated at room temperature for 90 min., after which 200 µl of S1 digestion buffer (30 mM NaOAc, pH 4.6; 250 mM NaCl; 1 mM ZnSO$_4$; 2 µl of 0.5 mg/ml denatured calf thymus DNA and 0.3 µl of S1 nuclease enzyme, 400 units/µl) was added to each tube and incubation was continued for 1 hr at 37° C. Reactions were terminated by addition of 50 µl of S1 stop buffer (0.3M NaOAc, pH 4.6; 10 mM EDTA; and 0.2 µg/ml yeast RNA). Solutions were extracted twice with an equal volume of water saturated phenol followed by two extractions with an equal volume of chloroform: isoamyl alcohol (24:1). Finally, two volumes of ethanol (100%) were added and the mixtures were evaporated to dryness in a speed-vac (Savant). Dried pellets were counted (Cerenkov) and 20 µl of gel loading buffer (90% formamide, 1x TBE [100 mM Tris, 100 mM boric acid, 2 mM EDTA, pH 8.3]) were added to each tube. Samples were added per lane on a 15% polyacrylamide (acrylamide:bis acrylamide ratio=29:1), 7M urea gel. After electrophoresis the gel was exposed to Kodak XAR film for 19 hr at 4° C.

Results

The portion of the Vmw65 coding region which contains the AUG codon and flanking regions complementary to oligo 293, as well as the amino terminal 83% of the Vmw65 coding sequences, was cloned into pGEM expression vector as described in Materials and Methods. + strand RNA, transcribed from this construct in vitro, translated in a cell-free rabbit reticulocyte system to yield a polypeptide with an apparent mass in SDS acrylamide gels of 52 kilodaltons (KDa). This size is slightly larger than the value predicted from amino acid composition (45 kDa), and may be attributable to the high proline content of the polypeptide in the N-terminal 100 amino acid residues [18%, Pellett et al., Proc. Natl. Acad. Sci. U.S.A., 82m:5870 (1985)].

Figure 2:
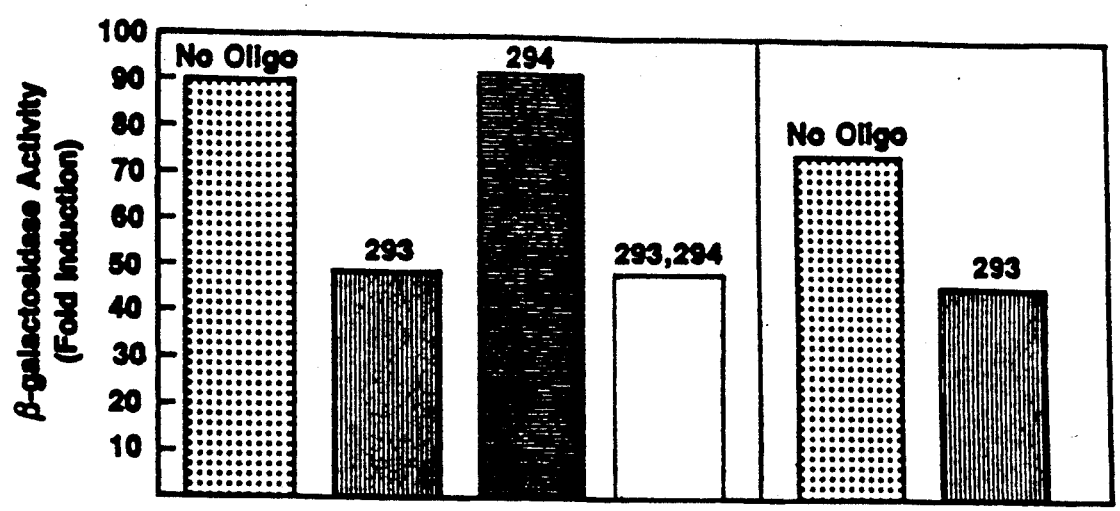
FIG. 2 illustrates complementary oligodeoxyribonucleotide inhibition of Vmw65 trans inducing activity in MTX5 cells. Results are depicted as fold induction of beta galactosidose activity in MTX5 cells after transfection with a plasmid DNA construct containing the bacterial lac Z gene under transcriptional control of the HSV-1 ICP4 promoter. Control levels are presented as no oligo (dotted) column. Cells exposed to oligo 293 (vertical stripes), oligo 294 (horizontal stripes), or both oligos (solid) at a concentration of 25 ug/ml of medium are shown for experiment 1. Only control and oligo 293 exposed cells were examined in experiment 2.

When oligo 293 was hybridized to pEM-2 transcript prior to in vitro translation of the mixture, decreased amount of truncated Vmw65 polypeptide was produced. The levels of translational inhibition were shown to be dependent upon the amount of oligo 293 present in the hybridization reaction (See Table 1). Analysis of the in vitro translation products by SDS PAGE revealed that the polypeptide products synthesized in the presence of lower amounts of oligo 293 were full length proteins and not products initiated at cryptic AUG codons located 3' of the oligo 293 target site (FIG. 2). Therefore, the estimates of translational inhibition in Table 1 were considered to be good approximations of specific (Vmw65 inhibition) and non-specific (BMV mRNA inhibition) inhibitory activity of the oligomer in this system.

TABLE 1

| In vitro inhibition of RNA translation by oligo 293 | | |
|---|---|---|
| Target RNA | Molar Ratio (oligo 293/RNA) | Inhibition (%) |
| pEM-2 | 500:1 | 14 |
| pEM-2 | 1000:1 | 48 |
| pEM-2 | 2000:1 | 71$^a$ |

TABLE 1-continued

| | In vitro inhibition of RNA translation by oligo 293 | |
|---|---|---|
| Target RNA | Molar Ratio (oligo 293/RNA) | Inhibition (%) |
| BMV | 2000:1 | 2.5[b] |

[a] % Inhibition is expressed as an average of values observed in 5 repeats of the experiment, the range was from 59–85% inhibition.
[b] % Inhibition is expressed as an average of values observed in 4 repeats of the experiment, the range was from 0.0–8.6% inhibition.

The observed specificity of oligo 293 inhibition suggested that the mechanism of inhibition involved an interaction of the oligomer with pEM-2 RNA rather than with the ribosomal apparatus. To examine this hypothesis, pEM-2 transcripts were hybridized with $^{32}$P-end labeled oligo 293 under conditions resembling the hybridization reaction performed prior to translation of RNA. The resultant hybrids were subjected to digestion with S1 nuclease and the products of the digestion were analyzed on acrylamide-urea gels. Oligo 293 which was hybridized to a molar excess of pEM-2 transcript was protected from digestion while nonhybridized oligo 293 was degraded by single strand specific nuclease. Hybridization of oligo 293 to pEM-2 transcript under the conditions used for hybrid arrest of translation (unlabeled oligo:$^{32}$P labeled oligo ratio=620:1) resulted in a diminished degree of oligo 293 protection from S1 digestion. Since the amount of pEM-2 transcript was constant for both hybridization reactions, it appears that the protection of oligo 293 from S1 nuclease digestion resulted from a molecular interaction between the two molecules which was decreased by the presence of excess unlabeled oligo 293.

EXAMPLE 2

Inhibition of Vmw65 Transactivational Activity with Complementary Oligodeoxynucleotide This example illustrates the ability of various 18-mer oligomers complementary to the initiation region for Vmw65 translation to inhibit the transient expression of protein (β-galactosidase) which is under the regulatory control of the Vmw65 transactivating protein.

Material and Methods

MTX5 cells were seeded into 96 well microtiter plates and allowed to grow to 80% confluency (approximately 80000 cells/well). One-half microgram of plasmid pON 105 DNA from Example 1 was introduced into the cells of each well by the DEAE dextran precipitation technique (Graham and Van der Eb, Virology, 52:456 (1973)]. Four to six hours later, the cells were rinsed with Hank's Balanced Salt Solution and overlaid with supplemented EMEM. At 48 hr post-transfection, the cells were assayed for beta galactosidase expression.

The level of beta galactosidase activity in each well was determined from cell lysates of the monolayer cultures. Determination of beta galactosidase activity was performed in 96 well microtiter plates. Aliquots were assayed by incubation in the presence of beta galactosidase substrate, 4-methylumbelliferyl-D-galactosidase (MUG, Sigma), for 2 hours. The generation of fluorescent product was quantified on a Microfluor microfluorimeter (Dynatech) after addition of 0.1M glycine, pH 10.3 [Spaete and Mocarski, J. Virol., 56:135 (1985)].

The effect of oligodeoxyribonucleotide on expression of Vmw65 activity was examined by growing MTX5 cells in the presence of 25 μg/ml oligodeoxyribonucleotide for two passages prior to the transfection of pON 105 plasmid DNA.

Results

As shown in FIG. 1, the nucleotide sequence around the translation initiation codon of Vmw65 mRNA is highly conserved among the different strains of HSV-1. We have synthesized two oligodeoxyribonucleotide fragments (18 mers) which are complementary to target sites within this region. The ability of these complementary oligomers to specifically inhibit the biological expression of the Vmw65 polypeptide was examined in MTX5 cells, which exhibit Vmw65 mediated activation of HSV immediate early promoter expression in the absence of viral superinfection [Kmetz et al., Nucleic Acids Res. 16:4735 (1988)]. Oligo 293 and oligo 294 (FIG. 1) were added to cell growth medium as described in Materials and Methods. The initial oligodeoxyribonucleotide concentration was chosen from literature values, which were shown effective in a similar system [Smith et al., Proc. Natl. Acad. Sci. U.S.A., 83:2787 (1986)]. The effectivenss of oligo 293 and oligo 294 in inhibiting Vmw65 activity in MTX5 cells is illustrated in FIG. 2. As seen, growth of cells in the presence of oligo 293, but not oligo 294, resulted in decreased level of HSV-1 ICP4 promoter expression, as judged by levels of indicator gene (beta galactosidase) activity in transfected cell cultures. The presence of both oligomers did not enhance the effect observed with oligo 293 alone. $^3$H-Leucine uptake levels suggest that total protein synthesis in MTX5 cells was not affected by the presence of oligodeoxyribonucleotides.

EXAMPLE 3

Inhibition of HSV Replication with Complementary Oligodeoxyribonucleotide

This example illustrates the inhibition of HSV replication by the oligomers that are complementary to the initiation region of mRNA coding for the transactivating protein Vmw65.

Methods and Materials

L TK-cells were seeded at $1.5 \times 10^6$ cells per 25 cm$^2$ T flask. Cells were overlaid with 5 ml of EMEM supplemented with glutamine, penicillin, streptomycin and 10% fetal calf serum, and incubated at 36.5° C. for 18–24 h. Where appropriate, oligo 293 was present in overlay medium. Following the incubation, cells were rinsed with Hank's Balanced Salt Solution and infected with HSV suspended in 1 ml of serum free EMEM. Virus and cells were incubated at 36.5° C. for 1 hour, with occasional rocking. Following adsorption, 4 ml of medium (EMEM+2% fetal bovine serum) containing appropriate concentrations of oligodeoxyribonucleotide were added to each flask and the cells were incubated either 24 hours (1 plaque forming units/cell) or 48 hours (0.5 plaque forming units/cell).

Cells were harvested in medium and centrifuged at 650× g at 4° C. for 10 min. Supernatants were recentrifuged at 20000×g at 4° C. for 30 min. Cell pellets were combined and resuspended in 1.5 ml of 15% fetal calf serum, 10% glycerol in EMEM. The suspension was frozen and thawed four times and stored at 80° C. in 0.3 ml aliquots. Virus titer was determined by plaque assay on Vero cell monolayers. Dilutions of each virus preparation were adsorbed as above, after which the virus inoculum was removed by aspiration and cells were overlaid with 3 ml of EMEM containing 2% fetal bovine serum (FBS) and 1.5% methylcellulose. Cells were incubated at 4° C. for 72 hours before plaques were counted.

Results

Having demonstrated the inhibition of Vmw65 transactivational function by oligo 293, we next examined the ability of this oligomer to inhibit replication of HSV in tissue culture. When L TK-cells were pretreated with oligo 293, infected with HSV, then incubated in the presence of oligodeoxyribonucleotide, yields of infectious virus were reduced 50–82% as compared to control levels produced in untreated (no oligo) cells (Table 2). The yields of infectious virus and levels of oligo 293 inhibition vary between experiments. This variation may be a reflection of subtle differences in virus titer applied to the monolayers. Indeed, infection of L TK-cells at higher multiplicity of infection (MOI=1) overcame the observed inhibition by oligo 293. A dose response study of oligo 293 inhibition was performed and the results are presented in Table 3. As indicated, the antiviral effect of oligomer was observed at levels of oligodeoxyribonucleotide in cell medium as low as 0.25 μg/ml. The antiviral activity of oligo 293 remained relatively constant between concentrations of 1.25 to 25 μg/ml. This plateau in activity probably reflects a limit in the intracellular uptake of available oligonuleotide from the medium.

TABLE 2

| Effect of complementary oligonucleotide on yield of infectious HSV. | | |
|---|---|---|
| | Virus yield (plaque forming units/ml) | Reduction |
| Experiment | without oligo 293 | with oligo 293 | % |
| HSV-1 | | | |
| 1 | $1.2 \times 10^5$ | $2.7 \times 10^4$ | 82 |
| 2 | $7.6 \times 10^6$ | $3.0 \times 10^6$ | 60 |
| 3 | $6.0 \times 10^7$ | $3.0 \times 10^7$ | 50 |
| HSV-2 | | | |
| 1 | $1.9 \times 10^7$ | $6.5 \times 10^6$ | 66 |
| 2 | $5.5 \times 10^5$ | $2 \times 10^5$ | 64 |

All virus infections were performed at an MOI = 0.5 pfu/cell.

TABLE 3

| Inhibition of HSV replication at various concentrations of oligo 293. | | |
|---|---|---|
| Concentrations of Oligo 293 (ug/ml) | Virus Yield (plaque forming units/ml) | Inhibition (%) |
| 0.00 | $5.5 \times 10^7$ | — |
| 0.25 | $3.5 \times 10^7$ | 36 |
| 1.25 | $1.8 \times 10^7$ | 67 |
| 6.25 | $2.1 \times 10^7$ | 62 |
| 25.00 | $2.0 \times 10^7$ | 64 |

The above examples demonstrate the utility of using complementary oligodeoxyribonucleotides to specifically inhibit gene expression in tissue culture. The target gene was the virion tegument protein (Vmw65) of HSV, which serves as a transactivating factor during immediate early gene transcription [Campbell et al., J. Mol. Biol., 180:1 (1984)]. This transactivating function allowed quantification of the effect of complementary oligomers on Vmw65 levels in a Vmw65 expressing cell line. In this system, the transient expression of beta galactosidase is dependent upon transcriptional activation of the HSV-1 ICP4 promoter, located immediately upstream of the bacterial lac Z gene in plasmid pON 105 [Kmetz et al., Nucleic Acids Res. 16:4735 (1988)]. Oligodeoxyribonucleotides complementary to the predicted translation initiation codons [Pellett et al., Proc. Natl. Acad. Sci U.S.A., 82m:5870 (1985); Dalrymple et al., Nucleic Acids Res., 13:7865 (1985)] of the Vmw65 mRNA were used to inhibit Vmw65 synthesis. Only one of the two oligomers (293) was effective at inhibiting Vmw65 activity. In the absence of amino acid analysis of the N terminal portion of virally produced Vmw65 protein, this data is the best evidence that the 3' most AUG sequence is the functional initiation codon for this mRNA (See FIG. 2). The identification of the functional translation initiation codon for the Vmw65 mRNA is of obvious benefit in designing antiviral molecules which act at this site of gene expression.

As predicted from data in MTX5 cells and in vitro translations, complementary oligodeoxyribonucleotide can inhibit replication of HSV in tissue culture. Although this type of inhibitory activity has been described for HSV using the splice junction of ICP22 and ICP47 as the target [Smith et al., Proc. Natl. Acad. Sci. U.S.A., 83:2787 (1986)], our system exhibits superior activity (50% inhibition of virus growth at 150 nM oligo 293 [See Table 2] vs. 50% inhibition at 25 μM splice junction oligomer). At these levels of oligomer concentration, non-specific cell toxicity was negligible in both our study and that of Smith et al., Proc. Natl. Acad. Sci. U.S.A., 83:2787 (1986). Thus it would seem that complementary oligodeoxyribonucleotide can be targetted to specifically hybridize to the initiation region for Vmw65 translation and to inhibit viral gene expression without perpetrating serious harm to normal cellular functions.

All the references cited herein are hereby incorporated by reference for their pertinent teachings.

I claim:

1. An oligomer capable of hybridizing to the second translation initiation region downstream from the 5' end of messenger RNA coding for a herpes simplex virus Vmw65 transactivating protein and substantially inhibiting translation of such messenger RNA, which oligomer comprises bases substantially complementary to such translation initiation region linked by a backbone comprising ribose phosphate, deoxyribose phosphate, ribose alkylphosphonate, deoxyribose alkylphosphonate, ribose arylphosphonate or deoxyribose arylphosphonate.

2. The oligomer of claim 1 in which the backbone comprises deoxyribose phosphate or deoxyribose alkylphosphonate.

3. The oligomer of claim 1 which is an oligodeoxynucleotide having the sequence, from 5' to 3':

GTC CGC GTC CAT GTC GGC.

* * * * *